(12) United States Patent
Gandini

(10) Patent No.: US 8,584,675 B2
(45) Date of Patent: Nov. 19, 2013

(54) DEVICE FOR REMOVING PULMONARY SECRETIONS

(75) Inventor: Alessandro Gandini, Viganello (CH)

(73) Assignee: IPH Establishment, Vaduz (LI)

( * ) Notice: Subject to any disclaimer, the term of this patent is extended or adjusted under 35 U.S.C. 154(b) by 1160 days.

(21) Appl. No.: 12/459,641

(22) Filed: Jul. 6, 2009

(65) Prior Publication Data

US 2010/0012126 A1   Jan. 21, 2010

(30) Foreign Application Priority Data

Jul. 18, 2008   (IT) .............................. MI2008A1315

(51) Int. Cl.
*A61M 16/00*   (2006.01)
*A62B 9/06*   (2006.01)

(52) U.S. Cl.
USPC ............ 128/205.19; 128/205.13; 128/207.14

(58) Field of Classification Search
USPC ............. 128/205.19, 207.16–207.18, 200.24
See application file for complete search history.

(56) References Cited

U.S. PATENT DOCUMENTS

| | | | | |
|---|---|---|---|---|
| 3,646,933 A | * | 3/1972 | Monnier | 128/204.24 |
| 3,700,000 A | * | 10/1972 | Hesse et al. | 137/494 |
| 4,029,093 A | * | 6/1977 | Kohnke | 128/203.28 |
| 4,066,076 A | * | 1/1978 | Williamson | 128/204.25 |
| 4,071,025 A | * | 1/1978 | Kohnke | 128/205.13 |
| 4,167,184 A | * | 9/1979 | Kohnke | 128/205.13 |
| 4,268,460 A | * | 5/1981 | Boiarski et al. | 261/1 |
| 4,453,543 A | * | 6/1984 | Kohnke et al. | 128/203.28 |
| 6,408,846 B1 | * | 6/2002 | Ohki et al. | 128/203.15 |
| 7,089,942 B1 | * | 8/2006 | Grey | 128/207.14 |
| 2004/0244796 A1 | * | 12/2004 | Semeia | 128/204.26 |
| 2004/0255951 A1 | * | 12/2004 | Grey | 128/207.14 |
| 2008/0216836 A1 | * | 9/2008 | Ottestad | 128/204.28 |
| 2012/0222675 A1 | * | 9/2012 | Dunne et al. | 128/203.15 |

* cited by examiner

*Primary Examiner* — Stephen Crow
(74) *Attorney, Agent, or Firm* — Hedman & Costigan, P.C.; James V. Costigan; Kathleen A. Costigan

(57) ABSTRACT

A device for removing bronchopulmonary secretions of a patient provides for a duct, an expansion chamber and means for accelerating the exhaled air.

17 Claims, 3 Drawing Sheets

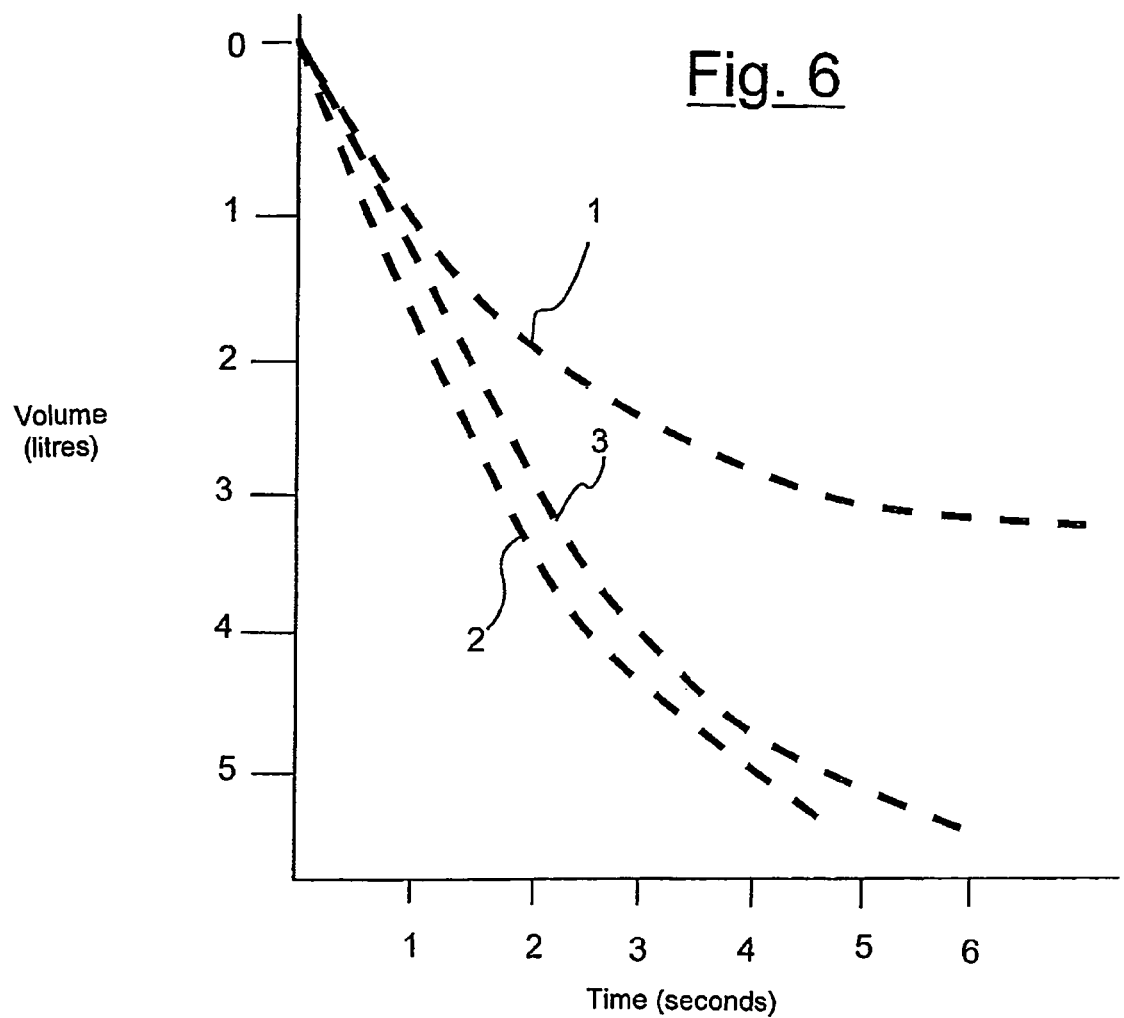

DEVICE FOR REMOVING PULMONARY SECRETIONS

Figure 1:
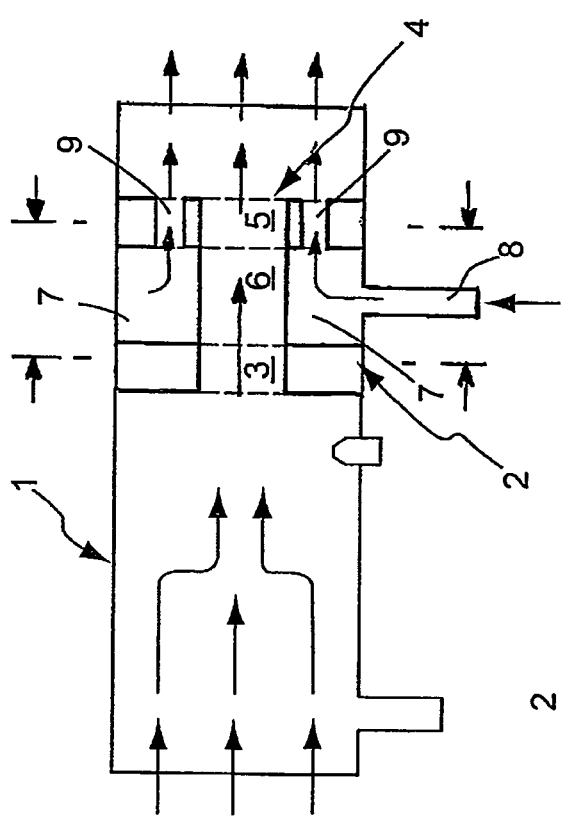

The present invention refers to a device for removing pulmonary secretions.

The present invention has its origins in the sector of the respiratory assistance devices for patients afflicted with pulmonary parenchyma pathologies, such as for example chronic obstructive bronchopneumopathy (COBP). In particular, the present invention concerns a device for the non-invasive removal of bronchopulmonary secretions in patients having reduced expectorant capacity.

In medicine, it has for some time been recognised that the incapacity to clean the lungs from the secretions considerably raises the risk of serious pathology development in patients, such as for example pneumonia and atelectasis. The incapacity to expectorate is also considered one of the main causes of complications in patients with respiratory insufficiency and reduced expectorant capacity due to neuromuscular pathologies (for example amyotrophic lateral sclerosis) or surgical operations in the abdomen or thorax.

In the presence of a reduced expectorant capacity, the patients are generally incapable of generating, while coughing, a pleural pressure sufficient for achieving the expectoration of the secretions.

According to the state of the art, different methods and devices are known and applied for removing the pulmonary secretions in patients afflicted with respiratory insufficiency. The known methods and devices essentially achieve an aspiration of the pulmonary secretions through an insufflation cycle of air in the lungs and subsequent exsufflation executed under suction. In such a manner, the secretions are suctioned from the lower part of the respiratory section towards the upper airways.

The removal of the secretions via aspiration according to the currently known techniques has various disadvantages. First of all, the devices used for such purpose are invasive and involve the insertion of endotracheal tubes, with consequent tracheal and larynx irritation. Secondly, the reduced pressure generated in order to suction the secretions involves a high risk of collapse of the airway walls, with consequent significant reduction, if not actual blocking, of the respiratory function. The collapse can also occur at the tissues constituting the palate, with the consequent induction of unpleasant sensations in the patient, who is obliged to frequently stop the functioning of the suction device. Finally, the aspiration of the secretions involves a forced ventilation of the lungs which interferes with the natural respiratory rhythm, which is specific for each treated patient.

Object of the present invention is that of identifying a device for removing bronchopulmonary secretions in patients with reduced expectorant capacity which allows overcoming the mentioned drawbacks of the state of the art.

Subject of the present invention is a device for removing bronchopulmonary secretions of a patient characterised in that it provides for a duct, an expansion chamber and means for accelerating the exhaled air.

In particular, the device according to the present invention comprises:
a) a duct connectable with the respiratory tracts of the patient;
b) an expansion chamber which provides for
b1) a first opening for the inflow of a gaseous current,
b2) at least one second opening through which the gaseous current exits from the expansion chamber and is inserted in the duct;
c) means for supplying the gaseous current inside the expansion chamber, where said means for accelerating the exhaled air are constituted by the gaseous current inserted in the duct.

Preferably, moreover, the exhaled air acceleration means are also constituted by the duct having a Venturi valve structure.

The functioning of the device according to the present invention is based on the non-invasive aspiration of the pulmonary secretions. The aspiration is made by establishing a moderate reduced pressure inside the duct connected with the respiratory tracts of the patient by means of a gaseous current. The gaseous current is inserted in the duct in which the air exhaled by the patient flows, so as to accelerate the latter towards the duct outlet.

The acceleration is achieved only during the expiratory phase, and its size is preferably proportional in every instant to the flow of air naturally exhaled by the patient. During the inspiratory phase, on the other hand, the device does not produce any effect on the inhaled air flow. The functioning of the device is therefore adapted to the natural rhythm of the patient's respiratory function.

The reduced pressure which is established in the duct connected with the respiratory tracts of the patient affects the entire pulmonary apparatus (alveoli, bronchi, etc.) and has a sufficient force for driving the secretions present therein towards the upper airways. The secretions, sliding on the water layer which covers the inner walls of the respiratory tracts, are first moved towards the central bronchi, and then climb the trachea, until they slide into the stomach through the oesophagus.

The duct is connectable to the respiratory tracts of the patient by means of a mouthpiece or nasal mask which conveys the air exiting from the mouth of the patient, avoiding dispersions.

At such mouthpiece, a sensor system is provided which detects both the presence and the intensity of the exhaled air flow and consequently activates the means for supplying the gaseous current inside the expansion chamber and subsequently inside the duct, i.e. activating the means for accelerating the exhaled air constituted by the gaseous current inserted in the duct.

Typically, the duct is a cylindrical tube of plastic material, but it can be made of other materials since it does not come into contact with the patient. Preferably, the duct has a Venturi valve type structure, i.e. it is a duct that has a narrowing ("narrow section") at least in one point of its length. The air flow exhaled from the patient flows inside the Venturi valve from the end with greater section towards the end with smaller section. In a duct of this type, the air flow encounters the narrow section and the crosses it, undergoing a first acceleration due to the Venturi effect.

The device according to the present invention moreover provides for an expansion chamber having a first opening through which it is possible to insert a gaseous current. The volume of the expansion chamber is variable, as a function of the quantity of gaseous current which one wishes to insert, and thus of the volumetric capacity of the pump.

The expansion chamber has at least one second opening which allows the gaseous current to exit and be inserted inside the duct. The gaseous current is inserted in the duct flowing parallel to its axis and in the same direction as the exhaled air flow, thus achieving a driving effect of the exhaled air towards the duct outlet.

In order to ensure a uniform acceleration of the exhaled air, the openings of the expansion chamber through which the gaseous current exit are preferably more than two, still more preferably at least 4.

Preferably, the expansion chamber has annular form and is developed around the duct.

A number of openings equal to at least 4 and the annular shape of the expansion chamber favour the uniform acceleration inside the duct of the air flow exhaled by the patient.

Figure 3:
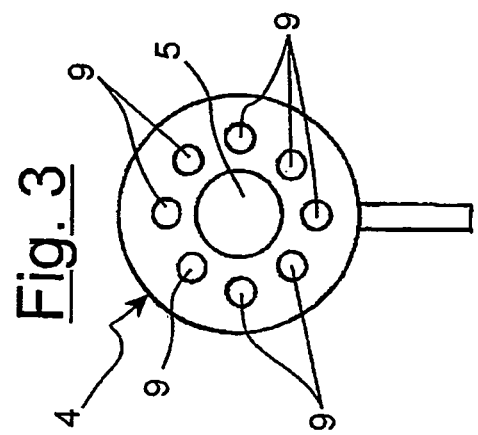
Figure 2:
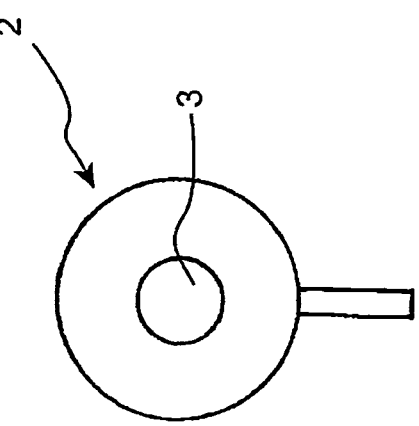
Figure 4:
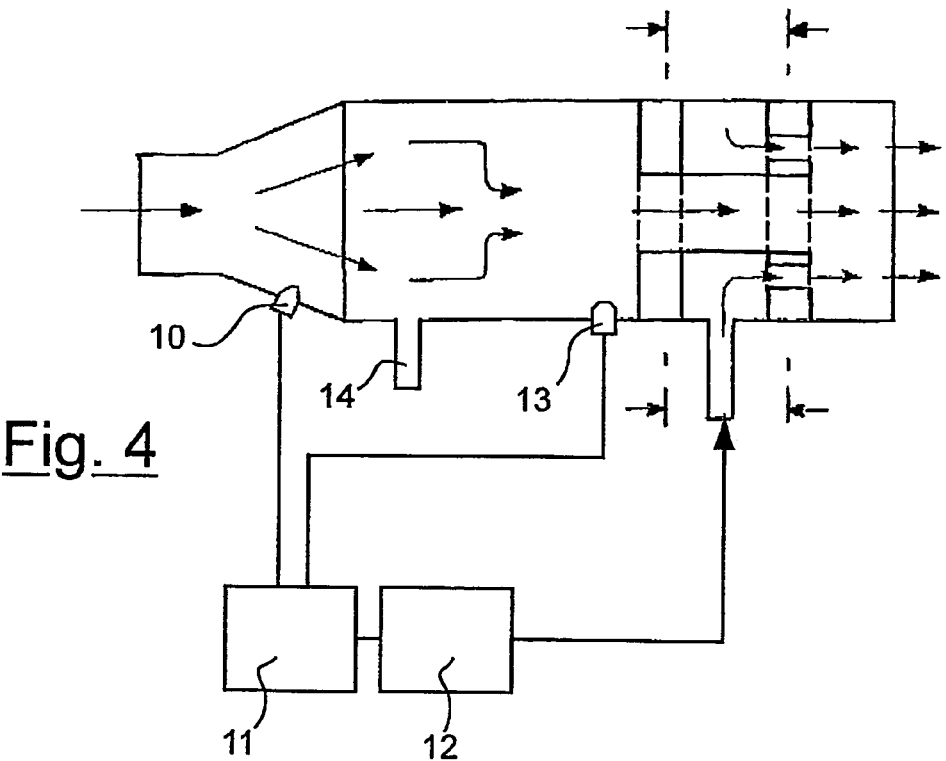
Figure 5:
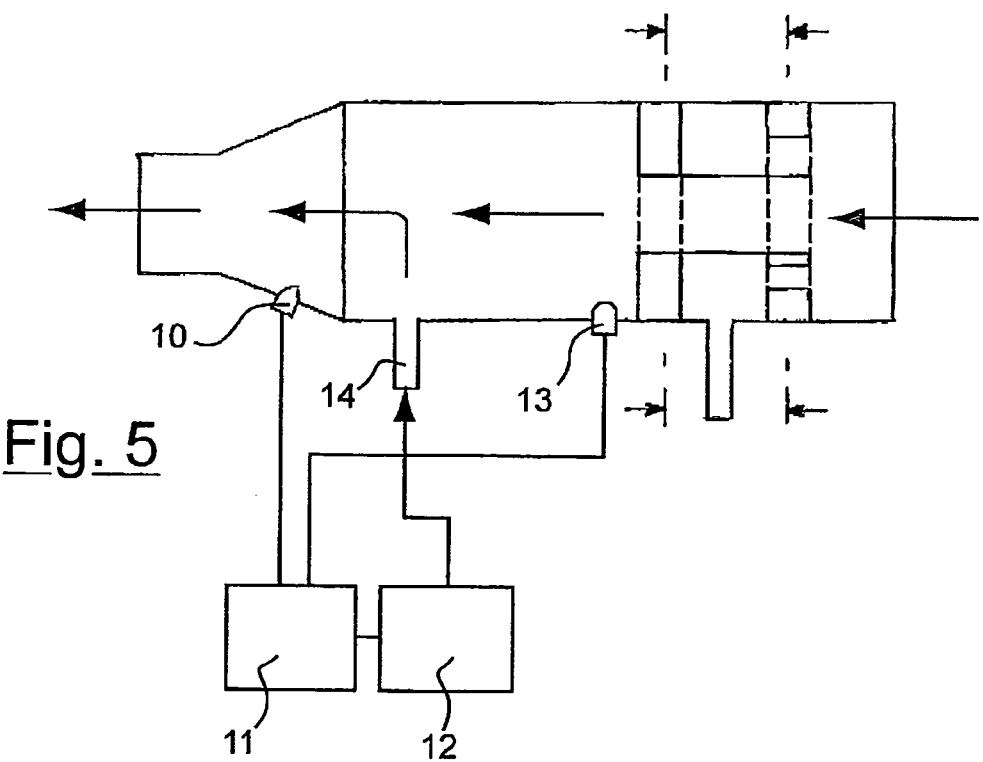

In a preferred embodiment of the device, subject of the present invention, the expansion chamber is made inside the duct in which the air exhaled and inhaled by the patient flows, as illustrated below with reference to the following figures:

FIG. 1: schematic cross-section of the device;

FIG. 2: schematic vertical section of the device along the trace II-II' of FIG. 1;

FIG. 3: schematic vertical section of the device along the trace III-III' of FIG. 1;

FIG. 4: schematic cross-section of the device (expiratory phase);

FIG. 5: schematic cross-section of the device (inspiratory phase);

FIG. 6: comparison between the spirometric curves.

The device which provides for the expansion chamber inside the duct consists of a main duct 1 inside of which, in an intermediate point between the inlet and outlet, a first closure plate 2 is positioned, having an opening 3 in order to allow the flow of the air exhaled and inhaled by the patient. The opening 3 has a section whose surface is less than that of the main duct 1. In an intermediate point between the first plate 2 and the outlet of the external duct, a second closure plate 4 is placed having at least one first opening 5 connected to the opening 3 of the plate 2 by means of a second duct 6 (secondary duct). The volume of space delimited by the main duct 1, by the secondary duct 6 and by the plates 2 and 4 constitutes an expansion chamber 7 of annular form.

In an intermediate point between the closure plates 2 and 4, an opening 8 is present through which it is possible to insert the gaseous current in the expansion chamber.

The plate 4 is provided with at least a plurality of openings 9 arranged in a circular ring, through which the gaseous current inserted in the expansion chamber can be inserted into the main duct, inside of which it achieves the driving action of the exhaled air flow.

In order to achieve the acceleration of the exhaled air flow, the flow rate of the gaseous current inserted in the duct is greater than that of said flow. The flow rate of the inserted gaseous current can be maintained constant or it can vary during the exhalation phase. Preferably, the flow rate of the gaseous current varies as a function of the quantity of air exhaled by the patient: the greater the air exhaled by the patient, the greater the flow rate will be of the inserted gaseous current, and thus the greater the acceleration imparted to the exhaled air.

This is made possible by the system of sensors present in the mouthpiece, which detect both the presence and the intensity of the exhaled air flow and consequently activate the means for supplying the gaseous current inside the expansion chamber, preferably consisting of a pump.

The flow rate of the inserted gaseous current can range from 0.1-100 l/s, preferably from 0.1-5 l/s, still more preferably from 0.1-1 l/s.

The flow rate of the inserted gaseous current can be adjusted from time to time to the most suitable value, according to the specific respiratory capacity of each patient. Such regulation is maintained constant during the functioning of the device.

Due to the acceleration of the exhaled air, in the duct section upstream of the point in which there is the inflow of the gaseous air coming from the exhalation chamber, reduced pressure is generated which induces the removal of the pulmonary secretions.

When the expiratory phase is terminated, and the inspiratory phase begins, the inflow of the gaseous current in the duct is blocked in order to allow the outside air to flow into the duct and reach the lungs of the patient.

In order to assist the patient in the inspiratory phase, a moderate air flow (about 18 liters per minute) or a flow of another breathable gas (positive inspiratory pressure—PIP) can be inserted in the duct, through a suitable opening. The device according to the present invention preferably comprises, as means for supplying a gaseous current inside the chamber, a gaseous fluid pump. The gaseous current is preferably composed of air. Nevertheless, it is possible to use any other gas or gas mixture compatible with the possibility of being accidentally inhaled by the patient.

In a particularly preferred embodiment of the device, subject of the present invention, it is possible to make the device functioning automatically, in particular the activation and deactivation of the inflow of the gaseous current in the expansion chamber. For such purpose, the device comprises, as observed above, a flow sensor 10 and control means 11 for activating the gaseous current supply means. The flow sensor 10 is positioned on the duct, or on the mouthpiece (FIG. 4) or nasal mask connected thereto, preferably near the mouth of the patient so it can quickly detect the beginning of the expiratory phase.

The sensor 10 generates a positive signal in the presence of an exhaled air flow, or a negative signal in the presence of an inhaled air flow. The generated signal is sent to the control means 11, which are functionally connected both with the sensor 10 and with the gaseous current supply means, for example a pump 12 (FIG. 4).

Preferably, at least the intensity of the positive signal, i.e. the signal generated during the expiratory phase, is proportional to the air flow exhaled by the patient.

In response to a positive signal of the sensor 10, the control means 11 activate the pump 12 which supplies the gaseous current into the expansion chamber. Consequently, with the establishment of the expiratory phase, the device begins to accelerate the air exhaled by the patent, favouring the removal of the pulmonary secretions. If the intensity of the signal generated by the sensor 10 is proportional to the exhaled air flow, the flow rate of the gaseous current inserted in the expansion chamber can be conveniently regulated by the control means 11 as a function of the exhaled air. In such a manner, the level of acceleration produced by the device will in every instant be proportional to the exhaled air flow. Therefore, the greater the quantity of air exhaled by the patient, the greater the quantity of gaseous current inserted by the pump 12 and, consequently, the greater the pulmonary secretion removal effectiveness.

In the concluding phase of the exhalation, the exhaled air flow progressively decreases until it is cancelled at the transition to the subsequent inhalation phase. With the beginning of the inhalation phase, the sensor 10 detects the reversal of the air flow direction in the duct, generating a negative signal which is sent to the control means 11.

In response to the negative signal of the sensor 10, whose intensity can be proportional (or not proportional) to the flow of air inhaled by the patient, the control means 11 deactivate the gaseous current supply, allowing a natural inhalation by the patient through the duct. Optionally, in order to assist the patient in the inhalation phase, the control means 11 in response to the negative signal of the sensor 10 also activate the inflow of a moderate PIP of air or another breathable gas through the opening 14 (for example at about 18 liters per minute).

In order to more accurately control the device action, and in particular to prevent the reduced pressure induced inside the respiratory tracks of the patient from reaching excessive levels, causing for example the collapse of the lung walls, the device can also comprise a pressure sensor 13 capable of detecting the reduced pressure that is generated in the duct due to the acceleration of the exhaled air by the inserted gaseous current. The pressure sensor 13 is positioned upstream of the gaseous current inflow point and is functionally connected to the control means 11 which activate/deactivate the supply of the gaseous current to the expansion chamber.

When a reduced pressure value greater than a specific threshold value is reached inside the duct, the pressure sensor 13 generates a signal, possibly of intensity proportional to the reduced pressure level, which is sent to the control means 11. The control means 11 block the supply of the gaseous current or reduce its flow rate until the reduced pressure is brought back below the threshold value.

The threshold value can be conveniently set as a function of the natural respiratory capacity of the patient.

The device according to the present invention offers various advantages with respect to the known state of the art devices. First of all, it allows obtaining an effective removal of the pulmonary secretions in patients having reduced expectorant capacities. Secondly, being a device of non-invasive type, it allows avoiding the problems connected with the use of endotracheal tubes. Moreover, the device, subject of the present invention, is capable of synchronously operating with the natural rhythm of the patient's respiratory function, i.e. supporting the natural alternation of the exhalation and inhalation phases. The removal of the pulmonary secretions therefore occurs without interfering with the normal expansion/compression action of the lungs. In addition, since its action can be regulated as a function of the air flow exhaled by the patient, the device is well adapted for use on patients with respiratory functionalities having even quite different capacities. The device allows preventing the phenomena of collapse of the walls of the respiratory tracts, due to their excessive emptying, as well as other side effects (unpleasant sensations, coughing attacks, etc.).

The characteristics and advantages of the process according to the present invention will be more evident from the following description, which is exemplifying and non-limiting of the protective scope defined by the enclosed claims.

EXAMPLE 1

A patient affected by COBP was treated with a device, subject of the present invention, according to the embodiment illustrated in FIG. 4.

The device operated with a gaseous current consisting of air. During its functioning, the flow rate of the gaseous current varied from 0-0.6 l/s. The treatment lasted 15 minutes.

In FIG. 6, the spirometric curves are compared of the patient before treatment with the device according to the present invention (curve 1), after the treatment with the device according to the present invention (curve 2) and the curve of a healthy subject. From a comparison of the curves 1-3, it is evident that the respiratory functionality of the patient affected by COBP considerably improves after treatment, reaching values very close to those observed in a healthy subject.

During treatment, an effective removal was observed of the small airway secretions, along with their being driven up to the stomach.

The treatment did not produce side effects, such as unpleasant sensations for the patient or cough attacks.

The invention claimed is:

1. Device for removing bronchopulmonary secretions of a patient comprising a duct, an expansion chamber, exhaled air accelerating means, a flow sensor for generating a positive signal in the presence of an exhaled air flow in the duct or a negative signal in the presence of an inhaled air flow; a gaseous current supply control activating means in response to the positive signal coming from the flow sensor and a gaseous current supply control deactivating means in response to a negative signal.

2. Device according to claim 1, comprising:
   a) a duct connectable with the respiratory tracts of the patient;
   b) an expansion chamber which provides for
      b1) a first opening for the inflow of a gaseous current,
      b2) at least a second opening through which the gaseous current exits from the expansion chamber and is inserted into the duct; and
   c) a gaseous current supplying means inside the expansion chamber, where said exhaled air accelerating means, are the gaseous current inserted in the duct.

3. Device according to claim 1, wherein the exhaled air accelerating means is a Venturi valve structure in said duct.

4. Device for removing bronchopulmonary secretions of a patient comprising a duct, an expansion chamber, exhaled air accelerating means, and a pressure sensor for generating a signal in the presence of reduced pressure in the duct when said reduced pressure is above a specific non-zero threshold value.

5. Device according to claim 1, wherein the duct is connected to a mouthpiece.

6. Device according to claim 1, wherein the duct is connected to a nasal mask.

7. Device according to claim 2, wherein the gaseous current supply is supplied by a pump.

8. Device according to claim 1, wherein the expansion chamber is an annular chamber having two or more openings for the exit of the inserted gaseous current.

9. Device according to claim 1, wherein the duct is connectable with the respiratory tracts of the patient and said duct has an opening through which a flow of air or other breathable gas is inserted.

10. Device according to claim 4, wherein the duct is connected to a mouthpiece.

11. Device according to claim 4, wherein the duct is connected to a nasal mask.

12. Device according to claim 4, wherein the expansion chamber is an annular chamber having two or more openings for the exit of the inserted gaseous current.

13. Device according to claim 4, wherein the duct is connectable with the respiratory tracts of the patient and said duct has an opening through which it is possible to insert a flow of air or other breathable gas.

14. Device according to claim 4 comprising:
   a) said duct is connectable with the respiratory tracts of the patient;
   b) said expansion chamber which provides for
      b1) a first opening for the inflow of a gaseous current,
      b2) at least a second opening through which the gaseous current exits from the expansion chamber and is inserted into the duct; and c) a gaseous current suurqina means inside the expansion chamber, where said exhaled air accelerating means are the gaseous current inserted in the duct.

15. Device according to claim 14 wherein the exhaled air accelerating means is a Venturi valve structure in said duct.

16. Device according to claim 1, wherein the expansion chamber is an annular chamber having at least four openings for the exit of inserted gaseous current.

17. Device according to claim 4, wherein the expansion chamber is an annular chamber having at least four openings for the exit of inserted gaseous current.

* * * * *